United States Patent [19]
Roulier et al.

[11] Patent Number: 6,045,814
[45] Date of Patent: *Apr. 4, 2000

[54] COSMETIC USE OF A RIGID GEL, AND COSMETIC OR DERMATOLOGICAL COMPOSITIONS THEREFOR

[75] Inventors: Veronique Roulier, Paris; Myriam Mellul, L'Hay-les-Roses; Therese Daubige, Bray-sur-Seine, all of France; Katrin Holz, Lausanne, Switzerland

[73] Assignee: L'Oreal, France

[*] Notice: This patent issued on a continued prosecution application filed under 37 CFR 1.53(d), and is subject to the twenty year patent term provisions of 35 U.S.C. 154(a)(2).

[21] Appl. No.: 09/068,196
[22] PCT Filed: Oct. 21, 1996
[86] PCT No.: PCT/FR96/01642
    § 371 Date: Aug. 20, 1998
    § 102(e) Date: Aug. 20, 1998
[87] PCT Pub. No.: WO97/17055
    PCT Pub. Date: May 15, 1997

[30] Foreign Application Priority Data

Nov. 6, 1995 [FR] France .................................. 95 13095

[51] Int. Cl.⁷ ............................... A61K 7/00; A61K 7/42; A61K 7/025; A61K 7/32; A61K 9/00
[52] U.S. Cl. .............................. 424/401; 424/59; 424/64; 424/65; 424/70.1; 424/400; 424/484; 514/944
[58] Field of Search .................... 424/400, 401, 424/59, 484, 64, 65, 70.1; 514/944

[56] References Cited

U.S. PATENT DOCUMENTS 3,615,972  10/1971  Morehouse, Jr. et al. ............... 156/79
5,034,216  7/1991  Barone et al. ............................ 424/63
5,612,043  3/1997  Deprez et al. .......................... 424/401
5,635,171  6/1997  Nadaud ................................ 424/78.03

FOREIGN PATENT DOCUMENTS

| 0 056 219 | 7/1982 | European Pat. Off. . |
| 0 412 865 | 2/1991 | European Pat. Off. . |
| 0 651 991 | 5/1995 | European Pat. Off. . |
| 651991 | 5/1995 | European Pat. Off. . |
| 664112 | 7/1995 | European Pat. Off. . |
| 2 715 306 | 7/1995 | France . |
| 43 20 401 | 12/1994 | Germany . |

OTHER PUBLICATIONS

Derwent Abstract of JP 60 081 120, "Cosmetic Preparation—Self Crosslinked Sodium Polyacrylate", Derwent Publications, (1985).

*Primary Examiner*—Shelley A. Dodson
*Assistant Examiner*—Marina Lamm
*Attorney, Agent, or Firm*—Finnegan, Henderson, Farabow, Garrett & Dunner, L.L.P.

[57] ABSTRACT

The present invention relates to the use in cosmetics of rigid gels containing at least 20% by weight of one or more water-soluble or hydrophilic gelling agent(s) which may be obtained from the said water-soluble or hydrophilic gelling agent in the presence of water by mixing, blending, compression and extrusion in a twin-screw extruder.

These gels constitute novel pharmaceutical forms for cosmetic or dermatological use. These gels are generally in the form of sticks, pencils or cakes. They may be aqueous with a matrix consisting of an aqueous gelled network. They may be in anhydrous form with a matrix consisting of a dehydrated gelled network. They may constitute many products in solid form applied to making up, to care of and/or to treatment of the skin, the scalp, the hair or the mucous membranes, or alternatively applied to the hygiene of the body, the skin, the scalp, the hair or the mucous membranes.

51 Claims, No Drawings

COSMETIC USE OF A RIGID GEL, AND COSMETIC OR DERMATOLOGICAL COMPOSITIONS THEREFOR

The present invention relates to the use, as cosmetic products, of rigid gels which may be obtained by extrusion, as well as to the cosmetic and dermatological compositions used.

Various forms of products in solid form are known in the cosmetics industry, in particular in the field of make-up, for instance lipsticks, foundation sticks or eyeshadow sticks; in the field of skincare or lipcare, such as lip-repairing pencils and depigmenting, make-up-removing or moisturizing sticks; in the field of hygiene, for instance deodorant sticks and foaming cakes or sticks for shaving or for washing the skin.

The Applicant has discovered, surprisingly, novel compositions for cosmetic or dermatological use in the form of a rigid gel which may be obtained by an extrusion process.

Throughout the description, the expression rigid gel will be understood to refer to any gel having a compression strength of greater than or equal to 50 grams, at room temperature, after penetration by a cylindrical probe having a diameter of 0.8 cm into the gel matrix in a thickness of 5 mm, at a speed of 1 mm/s, maintenance of the said probe in the gel matrix for 15 seconds and removal of the said probe from the gel matrix at a speed of 1 mm/s, the compression strength being measured with a texture analyser of the type TAXT2 marketed by the company Rheo.

The compositions according to the invention may be in the form of a stick, a pencil or a cake and may in themselves constitute novel types of make-up products such as lipsticks, foundations, eyeshadows; novel types of care and/or conditioning products for the hair such as hard styling gels; novel types of products in stick form for facial or body care or hygiene.

The compositions according to the invention may be aqueous and have a matrix consisting of an aqueous gelled network. They may also be in anhydrous form with a matrix consisting of a dehydrated gelled network.

The aqueous compositions according to the invention may be partially rehydratable at the surface in contact with water at the time of use, thereby allowing good release of the cosmetically active products onto the keratin substance to be treated, and, after drying, rapidly resuming their initial solid form without any adverse change occurring. They may thus be reused subsequently by simple partial hydration at the surface. In the resting state, they are stable on storage and do not feel sticky.

The aqueous compositions of the invention may in particular constitute compositions in the form of make-up sticks which, unexpectedly, impart the colour effect, the sensation of freshness and the slippery feel directly to the skin without it being necessary to incorporate large amounts of fatty substances. In addition, they produce no greasy effect or sticky feel when they are applied, or any phenomenon of migration into the wrinkles on the face or at the edge of the eyelids, in contrast with conventional make-up sticks containing large concentrations of fatty substances (oils or waxes) for the purpose of obtaining the colour effect and the slippery feel. They may, moreover, contain water-soluble cosmetic or dermatological active agents which cannot be incorporated into common, generally anhydrous make-up sticks.

The compositions according to the invention may contain enough inorganic fillers and/or organic fillers to give satisfactory breakdown and qualities of softness.

The production of sticks whose matrix consists of an aqueous gelled network, of sufficiently high rigidity, requires the presence of at least one water-soluble gelling agent in high concentrations, generally greater than 20% by weight. Hitherto, it was not possible to manufacture such solid aqueous gels by the conventional techniques such as manufacture by casting.

The Applicant has discovered, unexpectedly, that homogeneous, stable, rigid sticks, whose gelled matrix may contain more than 20% by weight of water-soluble gelling agent and large amounts of fillers, can be produced according to an extrusion process which will be defined later.

The compositions according to the invention, in particular the anhydrous compositions having a matrix consisting of a dehydrated gelled network, make it possible to produce make-up powders which may contain, in large amounts, waxes which impart good film strength, slippery feel and matt-effect properties. This fact is all the more surprising since conventional compacted make-up powders generally cannot contain large amounts of fatty substances such as waxes (more than 10% by weight). Their incorporation into powders leads to products which wax and which cannot be broken down.

The compositions can also contain silicone gums which are generally difficult to incorporate homogeneously at the same time into the anhydrous phases and into the aqueous phases.

The compositions according to the invention, in particular the anhydrous compositions having a matrix consisting of a dehydrated gelled network, may furthermore contain large amounts of fillers which are not readily compacted, thereby imparting a very soft and non-greasy feel. The expression filler which is not readily compacted is understood to mean a starting material which, at and above a certain percentage which will depend on the material in question, cannot be compacted by means of a mechanical press. These types of filler cannot be used in large concentrations in make-up products in compacted powder form. Furthermore, make-up products containing them, even in small amounts, do not exhibit good integrity on storage, good impact strength or a suitably flat surface.

The compositions of the invention, in particular the anhydrous compositions having a matrix consisting of a dehydrated gelled network, may be used in the form of a compact powdery stick, for instance a conventional make-up powder, without presenting the drawbacks mentioned above. These anhydrous compositions may also be reduced to a powder and may be used conventionally as a make-up powder without presenting the drawbacks mentioned above.

The compositions according to the invention are rigid gels containing, in a cosmetically acceptable medium, at least 20% by weight of at least one water-soluble or hydrophillic gelling agent and at least one cosmetic or dermatological substance. These rigid gels may be obtained from the said gelling agent in the presence of water, by mixing, blending, compression and extrusion in a twin-screw extruder.

These rigid gels are either in aqueous form and have a matrix consisting of an aqueous gelled network or are in anhydrous form with a matrix consisting of a dehydrated gelled network, and may be obtained by dehydration of the gelled network by a conventional drying process.

The rigid gels according to the invention generally have a compression strength of greater than or equal to 50 grams, at room temperature, after penetration by a cylindrical probe having a diameter of 0.8 cm into the gel matrix in a thickness of 5 mm, at a speed of 1 mm/s, maintenance of the said probe in the gel matrix for 15 seconds and removal of the said probe from the gel matrix at a speed of 1 mm/s, the compression strength being measured with a texture analyser of the type TAXT2 marketed by the company Rheo.

For the rigid gels in accordance with the invention, a curve relative to the rigidity of the gel and to the deposition of the gel on the probe as a function of time is preferably observed, under conditions as defined above, this curve having a positive peak corresponding to the compression force of the gel after penetration of the probe but having no negative peak corresponding to a deposition of gel onto the probe after it is removed.

The compositions according to the invention contain one or more water-soluble or hydrophillic gelling agents.

The water-soluble or hydrophillic gelling agents present in the compositions of the invention are preferably chosen from the group formed by:

alga extracts such as agar-agar, carrageenans and alginates;

seed extracts such as carob gum and guar gum;

plant exudates such as gum arabic, karaya gum, gum tragacanth and ghatti gum;

microorganism exudates such as xanthan gum, cellulose or its derivatives, for instance carboxymethylcellulose, hydroxypropylcellulose, methylcellulose, hydroxypropylmethylcellulose or hydroxyethylcellulose, and celluloses modified in particular by grafting an alkyl group;

fruit extracts such as pectins;

gelling agents of animal origin such as gelatin and caseinates;

water-soluble gelling synthetic polymers such as crosslinked polyacrylic acids such as "Carbopol" or "Pemulen" from the company Goodrich;

silicone derivatives such as synthetic hectorites, for instance the products "Laponite RD and RDS" sold by the company Waverly, and aluminium magnesium silicates, for instance the product "Veegum" sold by the company Vanderbilt.

The water-soluble or hydrophilic gelling agents are present in the compositions according to the invention, preferably, in concentrations ranging from 20 to 80% by weight relative to the total weight of the composition.

The compositions according to the invention may also contain inorganic fillers and/or organic fillers.

The fillers used in the compositions of the invention are cosmetic or dermatological particles that are insoluble in the medium formed by the starchy matrix.

The fillers are present in the compositions of the invention at concentrations ranging up to 80% by weight relative to the total weight of the composition, depending on the application chosen.

When the fillers are of very low density, in particular less than 0.1 g·cm$^{-3}$, they are preferably present in concentrations ranging up to 40% by weight relative to the final composition.

When the fillers are of higher density, in particular greater than 0.5 g·cm$^{-3}$, they are preferably present in a proportion of 2–80% by weight relative to the final composition.

The fillers used according to the invention are preferably chosen from inorganic or organic fillers, of lamellar or spherical structure, or mixtures thereof. They may be compactable or not readily compacted.

Each type of filler allows specific and different qualities to be imparted to the composition according to the invention. Thus, for example, fillers of inorganic lamellar type generally impart softness and a slippery feel; fillers of inorganic spherical type generally impart good breakdown properties and organic spherical fillers generally have a structuring role and impart softness.

Among the fillers of inorganic lamellar type which may be mentioned are:

talcs or hydrated magnesium silicates, in the form of particles generally smaller than 40 μm;

micas or aluminosilicates of varied compositions, which are in the form of flakes from 2 to 200 μm in size, preferably 5–70 μm, and from 0.1 to 5 μm in thickness, preferably 0.2–3 μm, it being possible for these micas to be of natural origin (for example muscovite, margarite, roscoelite, lipidolite, biotite) or of synthetic origin. They are generally transparent and allow a satiny appearance to be imparted to the skin;

clays such as sericites, which belong to the same chemical and crystalline class as muscovite but whose organoleptic properties are similar to those of talc;

kaolin or hydrated aluminium silicate, which is in the form of particles of isotropic forms generally smaller than 30 μm in size, these particles possessing good properties of absorption of fatty substances;

boron nitrides.

These fillers are generally compactable.

However, among these fillers of inorganic lamellar type, some are not readily compacted. Mention may thus be made of:

certain talcs, such as "Talc K1" from the company Nippon or "Talc Extra Steamic OOS" from the company Luzenac;

certain sericites, such as "Sericite BC282" from the company Whittaker;

most titanium micas when they are used in a high percentage, among which mention may be made of the nanotitanium mica "Coverleaf PC 2055M" from the company Ikeda.

Among the fillers of compactable organic lamellar type which may be mentioned are tetrafluoroethylene polymer powders, such as "Fluon" from the company Montefluos, or "Hostaflonq" from the company Hoechst.

Among the fillers of organic lamellar type which are not readily compacted, mention may be made of the lauroyl-lysine "Aminhope LL-11" from the company Ajinomoto.

Among the fillers of compactable inorganic spherical type which may be mentioned are:

oxides of zinc and of titanium, generally used in the form of particles not exceeding a few micrometers in size (or even less than 1 μm in the case of titanium oxide), in particular spherical titanium dioxides such as "Spherititan" from the company Ikeda; these oxides have a creamy feel, good covering power and considerable opacity;

precipitated calcium carbonate which, in the form of particles greater than 10 μm in size, has a creamy feel and allows a matt appearance to be obtained;

magnesium carbonate and hydrocarbonate, which possess, in particular, fragrance-binding properties;

non-porous spherical silica, and hydroxyapatite.

Among the fillers of inorganic spherical type which are not readily compacted, mention may be made of:

silica microspheres with open porosity or, preferably, hollow silica microspheres such as "Silica Beads" from the company Maprecos, these microspheres advantageously being impregnated with a cosmetic active agent, and the glass or ceramic microcapsules "Macrolite" from the company 3M.

Among the fillers of compactable organic spherical type which may be mentioned are:

metal soaps derived from organic carboxylic acids having from 8 to 22 carbon atoms, preferably from 12 to 18 carbon atoms, for example zinc, magnesium or lithium stearate, zinc laurate and magnesium myristate; these soaps, generally present in the form of particles smaller than 10 μm in size, have a creamy feel and facilitate the adhesion of the powder to the skin;

powders of non-expanded synthetic polymers, such as polyethylene, polyesters (for example polyethylene isophthalate or terephthalate) and polyamides (for example nylon), in the form of particles smaller than 50 μm in size, which possess absorbent properties and allow a velvety appearance to be imparted to the skin;

powders of spheronized crosslinked or non-crosslinked synthetic polymers, for instance powders of polyacrylic or polymethacrylic acid, powders of polystyrene crosslinked with divinylbenzene and silicone resin powders, and powders of organic materials of natural origin, for instance starch octenylsuccinate sold under the name Dry Flow Plus by the company Amylum.

Among the fillers of organic spherical type which are not readily compacted, mention may be made of:

microporous polymer microspheres, which have a structure similar to that of a sponge; they generally have a specific surface of at least 0.5 m$^2$/g, and in particular of at least 1 m$^2$/g, the said specific surface having no upper limit other than that resulting from the practical possibility of producing microspheres of very high porosity: the specific surface may, for example, reach 1000 m$^2$/g or even more. Mention may be made of microspheres of acrylic polymers, such as those made of the crosslinked acrylate copolymer "Polytrap" from the company Dow Corning, and those made of polymethyl methacrylate "Micropearl M" or "Micropearl M 100" from the company Seppic; these microporous microspheres may advantageously be impregnated, in particular with cosmetic active agents: mention may be made, in this respect, of the microspheres of styrene-divinylbenzene copolymers sold under the tradename "Plastic Powder FPSQ" by the company Toshiki, which are impregnated with squalane which is an emollient cosmetic active agent;

polymer microcapsules which contain a single closed cavity and form a reservoir which may contain a liquid, in particular a cosmetic active agent; they are prepared by known processes such as those described in patents U.S. Pat. No. 3,615,972 and EP-A-056,219. They may be prepared, for example, as polymers or copolymers of monomeric acids, amines or esters containing ethylenic unsaturation, as urea-formaldehyde polymers, as vinylidene chloride polymers or copolymers; by way of example, mention may be made of microcapsules made of methyl acrylate or methyl methacrylate polymers or copolymers, or alternatively copolymers of vinylidene chloride and acrylonitrile; among the latter, those which contain 20–60% by weight of units derived from vinylidene chloride, 20–60% by weight of units derived from acrylonitrile and 0–40% by weight of other units such as units derived from an acrylic and/or styrene monomer will be indicated in particular; it is also possible to use acrylic polymers or copolymers which are crosslinked, for example in the case of polymers containing a carboxylic group, with diols acting as crosslinking agents; by way of example, mention may be made of the microcapsules made of vinylidene chloride/acrylonitrile copolymer "Expancel" from the company Casco Nobel, the microcapsules "Q-Max" from the company Q-Max and the microcapsules "3 M" from the company 3M.

The compositions according to the invention may also contain a fatty phase. This fatty phase may comprise oils and/or waxes of animal, plant, inorganic or synthetic origin, alone or as mixtures.

Among the oils which may be used, mention may be made of mink oil, turtle oil, soya oil, grapeseed oil, sesame oil, corn oil, rapeseed oil, sunflower oil, cotton oil, avocado oil, olive oil, castor oil, jojoba oil, groundnut oil; hydrocarbon oils such as liquid paraffins, squalane, petrolatum; fatty esters, such as isopropyl myristate, isopropyl palmitate, butyl stearate, hexyl laurate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl triisostearate or diglyceryl triisostearate; silicone oils such as polymethylsiloxanes, polymethylphenylsiloxanes, polysiloxanes modified with fatty acids, fatty alcohols or polyoxyalkylenes, fluoro silicones, perfluoro oils; higher fatty acids such as myristic acid, palmitic acid, stearic acid, behenic acid, oleic acid, linoleic acid, linolenic acid or isostearic acid; higher fatty alcohols such as cetanol, stearyl alcohol or oleyl alcohol.

Among the waxes which may be used, mention may be made of beeswaxes, lanolin waxes and Chinese waxes; carnauba wax, candelilla wax, ouricurry wax, cork fibre waxes, sugar cane waxes, Japan waxes, hydrogenated jojoba waxes and hydrogenated oils such as hydrogenated sunflower oil, hydrogenated castor oil, hydrogenated coconut oil and hydrogenated lanolin; paraffins, microcrystalline waxes, montan waxes and ozokerites; polyethylene waxes, waxes obtained by Fisher-Tropsch synthesis, waxy copolymers and esters thereof, and silicone waxes such as polyalkoxy and polyalkylsiloxanes.

The fatty phase is present in proportions preferably ranging up to 20% by weight and more particularly up to 15% by weight relative to the total weight of the composition, depending on the application chosen.

The fatty phase may also comprise additives such as lipophilic cosmetic active agents and/or liposoluble ingredients generally used in cosmetics, for instance fragrances. Preferably, these additives may be present in an amount ranging up to 20% relative to the total weight of the fatty phase.

The compositions according to the invention may also additionally contain one or more silicone gums which allow qualities of softness and slippery feel to be imparted to the final compositions and which are generally difficult to incorporate homogeneously at the same time into the anhydrous phases and into the aqueous phases.

Silicone gum having a molecular weight of less than 1,500,000, such as a polydimethylsiloxane, a polyphenylsiloxane or a polyhydroxysiloxane, is preferably used, alone or as a mixture.

In particular, use may be made of a silicone gum corresponding to the formula:

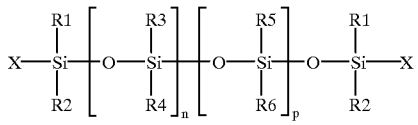

in which:

R₁, R₂, R₅ and R₆ are, together or separately, an alkyl radical having 1 to 6 carbon atoms, R₃ and R₄ are, together or separately, an alkyl radical having from 1 to 6 carbon atoms or an aryl radical, X is an alkyl radical having from 1 to 6 carbon atoms, a hydroxyl radical or a vinyl radical, n and p being chosen so as to impart a viscosity of greater than 100,000 mPa·s, preferably greater than 500,000 mPa·s, to the silicone gum.

n and p may generally take values from 0 to 5000, preferably from 0 to 3000.

The silicone gum may be introduced into the composition as it is or diluted in a silicone oil such as a PDMS (polydimethylsiloxane). As silicone gum which can be used according to the invention, mention may be made of those for which:

- the substituents R₁ to R₆ and X represent a methyl group, p=0 and n=2700, such as that sold under the name SE30 by the company General Electric,
- the substituents R₁ to R₆ and X represent a methyl group, p=0 and n=2300, such as that sold under the name AK 500000 by the company Wacker,
- the substituents R₁ to R₆ represent a methyl group, the substituent X represents a hydroxyl group, p=0 and n=2700 as a 13% solution in cyclopentasiloxane, such as that sold under the name Q2-1401 by the company Dow Corning,
- the substituents R₁ to R₆ represent a methyl group, the substituent X represents a hydroxyl group, p=0 and n=2700, as a 13% solution in dimethicone, such as that sold under the name Q2-1403 by the company Dow Corning,
- the substituents R₁, R₂, R₅, R₆ and X represent a methyl group and the substituents R₃ and R₄ represent an aryl group such that the molecular weight of the compound is 600,000, such as that sold under the name 761 by the company Rhône-Poulenc.

The silicone gums are present in concentrations preferably ranging up to 40% by weight, depending on the application chosen, and more particularly from 5 to 10% by weight relative to the total weight of the composition.

The compositions according to the invention may contain, besides the fillers, pigments, preferably in an amount ranging up to 50% relative to the total weight of the final composition. These pigments may be chosen from inorganic pigments, organic pigments and pearlescent pigments.

Among the inorganic pigments which may be mentioned, for example, are titanium dioxide (rutile or anatase), optionally surface-treated; black, yellow, red and brown iron oxides; manganese violet; ultramarine blue; chromium oxide, optionally hydrated; ferric blue.

Among the organic pigments which may be mentioned, for example, are the pigments D & C red, D & C orange, D & C yellow, carbon black and lakes based on cochineal carmine.

The pearlescent pigments may be chosen in particular from white pearlescent pigments such as mica coated with titanium oxide or bismuth oxychloride; coloured pearlescent pigments such as titanium mica with iron oxides, titanium mica with ferric blue or chromium oxide, titanium mica with an organic pigment of the abovementioned type, and pigments based on bismuth oxychloride.

The compositions according to the invention may also contain one or more non ionic, anionic, cationic or amphoteric surfactants usually used in cosmetics. The amount of surfactant used is preferably from 2 to 30% relative to the total weight of composition.

The aqueous compositions according to the invention may also additionally contain water-soluble cosmetic active agents.

Among the cosmetic active agents which may be mentioned are antioxidants or anti-free-radical agents; moisturizing or wetting agents such as glycerol and collagen; UV screening agents such as benzophenone. These water-soluble active agents may be present in the final composition in an amount ranging up to 20%, preferably 5 to 15%, by weight.

The present invention also relates to a process for the preparation of a composition as defined above, characterized in that this composition is obtained from one or more water-soluble or hydrophilic gelling agent(s) as defined above, the cosmetic or dermatological substance and optionally other ingredients as listed above, in the presence of water, by mixing, blending and extrusion in a twin-screw extruder.

The extruder used for the process of the invention is chosen from twin-screw extruders such as that described in application FR 94-00756.

The starting materials are introduced, at the twin-screw extruder inlet, into the supply zone at room temperature, preferably at about 20° C., and are then brought to the transportation zone at a temperature preferably of about 50° C., after which they are blended and compressed in various zones of the extruder maintained at a temperature preferably ranging from 60 to 100° C.; the mass obtained is transported to the extruder outlet and extruded through a die.

During the phase of blending and compressing, the water-soluble gelling agent in contact with the water forms, after extrusion, an aqueous gelled network which constitutes the matrix of the final products. The extruded mass leaves the die in the form of extrudates of given diameter depending on the die used, it being possible for these extrudates then to be cut up and shaped into sticks, aqueous-leaded pencils or solid cakes. Other forms may, of course, be produced by selecting suitable dies and devices for shaping the final products which are suited to the desired shape.

The compositions thus obtained have a matrix consisting of an aqueous gelled network. They may be made anhydrous by dehydration of the gelled network by a suitable standard drying process to give powdery compact products such as powdery sticks. The anhydrous solid compositions thus obtained may also be reduced to powder and used conventionally as make-up powders without exhibiting the drawbacks mentioned above.

The solid compositions according to the invention may be in various forms depending on the application chosen. The forms used most often are sticks, pencils and cakes.

The aqueous or anhydrous compositions according to the invention may be make-up products such as lipsticks, foundations, eyeshadows in aqueous gelled stick form or alternatively blushers, eyeshadows or concealers in powdery stick form. They may be applied directly onto the face.

The aqueous make-up compositions of the invention may, at the time of use, be partially rehydrated at the surface by contact with water in order to deliver the active substances for the make-up, and then, after drying, regain their initial form without any adverse change occurring, ready for another use under the same conditions.

Another subject of the invention is thus a process for making up the lips, the face, around the eyes, the cheeks or the eyelids, characterized in that a partially rehydratable aqueous solid composition as defined above is used, which composition is made moist at the surface with water and the said partially rehydrated composition is applied to the lips, the face, around the eyes, the cheeks or the eyelids.

The aqueous compositions according to the invention may also be care and/or conditioning and/or hygiene products for the skin, the mucous membranes, the scalp or the hair. They are generally in stick, pencil or cake form. They may in particular be applied to the keratin substances, at the time of use, by simple partial hydration at the surface in contact with water in order to deliver the active substances, and, after drying, regain their initial form without any adverse change occurring, ready for another use under the same conditions.

Among the care, conditioning or hygiene products which may be envisaged, mention may be made, for example, in hair care, of: solid styling gels in stick form; in skin care, of: make-up-removing products, moisturizing products or slimming products in stick or cake form and lipcare products in stick or pencil form; in hygiene, of: shampoos, shaving, bath or shower products, and deodorants, in stick or cake form.

Another subject of the invention consists of a cosmetic treatment process for care and/or conditioning and/or hygiene of the skin, the hair, the scalp or the mucous membranes, characterized in that an aqueous solid composition as defined above is used, which composition is made moist at the surface with water and the said partially rehydrated composition is applied to the skin, the hair, the scalp or the mucous membranes.

Another subject of the invention relates to the use of an anhydrous solid composition as defined above, as a make-up powder.

Obviously, a person skilled in the art will take care to select this or these possible complementary compounds and/or the amounts thereof such that the advantageous properties intrinsically associated with the composition in accordance with the invention are not, or are substantially not, adversely affected by the addition or additions envisaged.

The example which follows serves to illustrate the invention without, however, limiting the scope thereof.

EXAMPLE

Lipsticks to be Partially Rehydrated

The final product has the following formulation:

| | |
|---|---|
| Carob gum (water-soluble gelling agent) | 30.0% by weight |
| Water-soluble pigments | 10.0% by weight |
| Expanded particles of vinylidene chloride/acrylonitrile/methyl methacrylate copolymer sold under the name Expancel 550DE by the company Casco Nobel | 1.0% by weight |
| Silica sold under the name SB700 by the company Maprecos | 10.0% by weight |
| Preserving agent | 0.5% by weight |
| Water qs | 100.0% by weight |

PROCEDURE

The sticks are obtained by extrusion in a twin-screw extruder. The starting materials are introduced into the extruder inlet at a temperature of 30° C. They are then brought into the transportation zone at a temperature of 50° C. and are then blended and compressed in various zones of the extruder, which are maintained at 100° C. The mass thus blended and compressed is transported to the extruder outlet and extruded through a die 1 cm in diameter. The spin speed of the screws is 500 revolutions/minute. The extrudates obtained at the die outlet are reduced to sticks 3 cm in length using a cutting device at the extruder outlet.

We claim:

1. A process for preparing a cosmetic or dermatological composition in the form of a rigid gel comprising including in said cosmetic or dermatological composition at least 20% by weight of at least one water-soluble or hydrophilic gelling agent, wherein said composition in the form of a rigid gel is obtained by mixing, blending, compressing, and extruding said at least one gelling agent in the presence of water in a twin-screw extruder, and further wherein said composition in the form of a rigid gel has a compression strength of at least 50 grams at room temperature, and wherein said composition further comprises at least one pigment.

2. A process according to claim 1, wherein said composition is obtained by:
   a) introducing at least one water-soluble or hydrophilic gelling agent and water at the extruder inlet, at room temperature,
   b) bringing said at least one water-soluble or hydrophilic gelling agent and water to the transportation zone at a temperature of about 50° C.,
   c) blending and compressing said at least one water-soluble or hydrophilic gelling agent and water in various zones of the extruder maintained at a temperature ranging from 60 to 100° C.,
   d) transporting the mass obtained to the extruder outlet, and
   e) extruding said mass through a die.

3. A process according to claim 1, wherein said composition is aqueous and has a matrix comprising an aqueous gelled network.

4. A process according to claim 1, wherein said composition is made anhydrous by dehydration of the aqueous gelled network by a drying process.

5. A process according to claim 1, wherein said at least one water-soluble or hydrophilic gelling agent is selected from:
   alga extracts;
   seed extracts;
   plant exudates;
   microorganism exudates;
   fruit extracts;
   gelling agents of animal origin;
   water-soluble gelling synthetic polymers; and
   silicone derivatives.

6. A process according to claim 5, wherein said at least one water-soluble gelling agent or hydrophilic gelling agent is selected from: agar-agar, carageenans, alginates, carob gum, guar gum, gum arabic, karaya gum, gum tragacanth, ghatti gum, xanthan gum, celluloses, modified celluloses, pectins; gelatin, caseinates, crosslinked polyacrylic acids, synthetic hectorites and aluminium magnesium silicates.

7. A process according to claim 1, wherein said at least one water-soluble or hydrophilic gelling agent is present in an amount ranging from 20 to 80% by weight relative to the total weight of said composition.

8. A cosmetic or dermatological composition in the form of a rigid gel, said composition comprising at least 20% by weight of at least one water-soluble or hydrophilic gelling agent relative to the total weight of said composition and at least one additional cosmetic or dermatological ingredient, wherein said cosmetic or dermatological composition is obtained by mixing, blending, compressing, and extruding said at least one water-soluble or hydrophilic gelling agent and said at least one additional cosmetic or dermatological ingredient in the presence of water in a twin-screw extruder, and further wherein said composition in the form of a rigid gel has a compression strength of at least 50 grams at room temperature, and wherein said composition further comprises at least one pigment.

9. A cosmetic or dermatological composition according to claim 8, wherein said cosmetic or dermatological composition is obtained by:
   a) introducing said at least one water-soluble or hydrophilic gelling agent, said at least one additional cosmetic or dermatological ingredient and said water at the extruder inlet, at room temperature,
   b) bringing said at least one water-soluble or hydrophilic gelling agent, said at least one additional cosmetic or dermatological ingredient and said water into the transportation zone at a temperature of about 50° C.,
   c) blending and compressing said at least one water-soluble or hydrophilic gelling agent, said at least one additional cosmetic or dermatological ingredient and said water in various zones of the extruder maintained at a temperature ranging from 60 to 100° C.,
   d) transporting the mass obtained to the extruder outlet, and
   e) extruding said mass through a die.

10. A cosmetic or dermatological composition according to claim 8, wherein composition is aqueous and has a matrix comprising an aqueous gelled network, such that a solid aqueous gel composition is formed.

11. A cosmetic or dermatological composition according to claim 8, wherein said composition is made anhydrous by dehydration of the aqueous gelled network by a drying process.

12. A cosmetic or dermatological composition according to claim 8, wherein said at least one water-soluble or hydrophilic gelling agent is selected from:
   alga extracts;
   seed extracts;
   plant exudates;
   microorganism exudates;
   fruit extracts;
   gelling agents of animal origin;
   water-soluble gelling synthetic polymers; and
   silicone derivatives.

13. A cosmetic or dermatological composition according to claim 12, wherein said at least one water-soluble or hydrophilic gelling agent is selected from:
   agar-agar, carageenans, alginates, carob gum, guar gum, gum arabic, karaya gum, gum tragacanth, ghatti gum, xanthan gum, celluloses, modified celluloses, pectins;
   gelatin, caseinates, crosslinked polyacrylic acids, synthetic hectorites and aluminium magnesium silicates.

14. A cosmetic or dermatological composition according to claim 8, wherein said at least one water-soluble or hydrophilic gelling agent is present in an amount ranging from 20 to 80% by weight relative to the total weight of said composition.

15. A cosmetic or dermatological composition according to claim 8, wherein said composition further comprises at least one filler.

16. A cosmetic or dermatological composition according to claim 15, wherein said at least one filler is selected from inorganic and organic fillers.

17. A cosmetic or dermatological composition according to claim 15, wherein said at least one filler is present in an amount ranging up to 80% by weight relative to the total weight of said composition.

18. A cosmetic or dermatological composition according to claim 15, wherein said at least one filler has a density of less than 0.1 g·cm$^{-3}$ and is present at up to 40% by weight relative to the total weight of said composition.

19. A cosmetic or dermatological composition according to claim 15, wherein said at least one filler has a density of greater than 0.5 g·cm$^{-3}$ and is present in an amount ranging from 2 to 80% by weight relative to the total weight of said composition.

20. A cosmetic or dermatological composition according to claim 16, wherein said at least one filler is selected from inorganic and organic fillers of lamellar and spherical structures, which are compactable or not readily compacted.

21. A cosmetic or dermatological composition according to claim 20, wherein said inorganic lamellar fillers are selected from talcs, hydrated magnesium silicates, micas, aluminosilicates, clays, kaolin, hydrated aluminium silicate, and boron nitrides.

22. A cosmetic or dermatological composition according to claim 21, wherein said clays are selected from sericites.

23. A cosmetic or dermatological composition according to claim 21, wherein said micas are selected from titanium micas.

24. A cosmetic or dermatological composition according to claim 20, wherein said organic lamellar fillers are selected from tetrafluoroethylene polymer powders and lauroyl-lysine.

25. A cosmetic or dermatological composition according to claim 20, wherein said inorganic spherical fillers are selected from zinc oxides, titanium oxides, precipitated calcium carbonate, magnesium carbonate and hydrocarbonate, non-porous spherical silica, hydroxyapatite, silica microspheres with open or hollow porosity, optionally impregnated with a cosmetic active agent, and glass and ceramic microcapsules.

26. A cosmetic or dermatological composition according to claim 20, wherein said organic spherical fillers are selected from metal soaps derived from organic carboxylic acids having from 8 to 22 carbon atoms; non-expanded synthetic polymer powders; spheronized, crosslinked and non-crosslinked synthetic polymer powders; powders of organic materials of natural origin, microporous polymer powders optionally impregnated with cosmetic active agents; and optionally crosslinked polymer microcapsules.

27. A cosmetic or dermatological composition according to claim 26, wherein said metal soaps are selected from zinc, magnesium or lithium stearate, zinc laurate and magnesium myristate.

28. A cosmetic or dermatological composition according to claim 8, wherein said composition further comprises a fatty phase.

29. A cosmetic or dermatological composition according to claim 28, wherein said fatty phase is present in an amount up to 20% by weight relative to the total weight of said composition.

30. A cosmetic or dermatological composition according to claim 29, wherein said fatty phase is present in an amount up to 15% by weight relative to the total weight of said composition.

31. A cosmetic or dermatological composition according to claim 28, wherein said fatty phase comprises at least one oil or wax of animal, plant, inorganic or synthetic origin.

32. A cosmetic or dermatological composition according to claim 8, wherein said at least one additional cosmetic or dermatological ingredient comprises at least one adjuvant.

33. A cosmetic or dermatological composition according to claim 32, wherein said at least one adjuvant is selected from additional pigments, surfactants, liposoluble active agents, liposoluble additives conventionally used in cosmetics, antioxidants, anti-free-radical agents, moisturizers, wetting agents and sunscreens.

34. A cosmetic or dermatological composition according to claim 8, wherein said at least one additional cosmetic or dermatological ingredient comprises at least one silicone gum.

35. A cosmetic or dermatological composition according to claim 34, wherein said at least one silicone gum is present in an amount ranging up to 40% relative to the weight of said composition.

36. A cosmetic or dermatological composition according to claim 35, wherein said at least one silicone gum is present in an amount ranging from 5 to 10% relative to the weight of said composition.

37. A cosmetic or dermatological composition according to claim 34, wherein said at least one silicone gum is selected from silicone gums having a molecular weight of less than 1,500,000.

38. A cosmetic or dermatological composition according to claim 37, wherein said silicone gums are selected from polydimethylsiloxanes, polyphenylsiloxanes, polyhydroxysiloxanes, and gums corresponding to the formula:

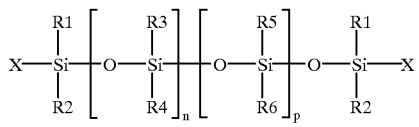

in which:
R$_1$, R$_2$, R$_5$ and R$_6$ together or separately represent an alkyl radical having from 1 to 6 carbon atoms,
R$_3$ and R$_4$ together or separately represent an alkyl radical having from 1 to 6 carbon atoms or an aryl radical, p1
X is an alkyl radical having from 1 to 6 carbon atoms, a hydroxyl radical or a vinyl radical,
n and p are selected so as to impart a viscosity of greater than 100,000 mPa·s to the silicone gum.

39. A cosmetic or dermatological composition according to claim 38, wherein n and p are selected so as to impart a viscosity of greater than 500,000 mpa·s to the silicone gum.

40. A cosmetic or dermatological composition according to claim 38, wherein n and p represent values ranging from 0 to 5000.

41. A cosmetic or dermatological composition according to claim 40, wherein n and p represent values ranging from 0 to 3000.

42. A cosmetic or dermatological composition according to claim 8, wherein said composition is in the form of a stick, a pencil or a cake.

43. A cosmetic or dermatological composition according to claim 8, wherein said at least one additional cosmetic or dermatological ingredient comprises at least one nonionic, anionic, cationic, or amphoteric surfactant.

44. A cosmetic or dermatological composition according to claim 43, wherein said at least one surfactant is present in an amount ranging from 2 to 30% relative to the total weight of said composition.

45. A cosmetic or dermatological composition according to claim 8, wherein said composition is a care product, a conditioning product, or a hygiene product for the skin, the mucous membranes, the scalp or the hair.

46. A cosmetic or dermatological composition according to claim 8, wherein said composition is a make-up product.

47. A make-up powder composition in the form of an anhydrous rigid gel with a matrix comprising a dehydrated gelled network, said composition containing at least one water-soluble or hydrophilic gelling agent, wherein said composition is obtained by mixing, blending, compressing, and extruding said at least one gelling agent in the presence of water in a twin-screw extruder, and further wherein said composition In the form of a riaid gel has a compression strength of at least 50 grams at room temperature, and wherein said composition further comprises at least one pigment.

48. A process for preparing a dermatological or cosmetic composition in the form of a rigid gel containing at least 20% by weight of at least one water-soluble or hydrophilic gelling agent, comprising mixing, blending, compressing, and extruding in a twin-screw extruder said at least one water-soluble or hydrophilic gelling agent and at least one additional dermatological or cosmetic ingredient, in the presence of water, optionally dehydrating said composition by a standard drying process, and wherein said composition in the form of a rigid gel has a compression strength of at least 50 grams at room temperature, and wherein said composition further comprises at least one pigment.

49. A process according to claim 48, wherein said at least one water-soluble or hydrophilic gelling agent, said at least one additional dermatological or cosmetic ingredient and water are introduced, at the extruder inlet, at room temperature, said at least one water-soluble or hydrophilic gelling agent, at least one dermatological or cosmetic ingredient and water are brought to the transportation zone at a temperature of about 50° C., said at least one water-soluble or hydrophilic gelling agent, at least one dermatological or cosmetic ingredient and water are blended and compressed in various zones of the extruder maintained at a temperature ranging from 60 to 100° C.; the mass obtained is transported to the extruder outlet and said mass is extruded through a die.

50. A cosmetic treatment process for the care, conditioning or hygiene of the skin, the hair, the scalp or the mucous membranes, comprising moistening the surface of an aqueous solid composition according to claim 10 with water to partially rehydrate said composition and applying said partially rehydrated composition to the skin, the hair, the scalp or the mucous membranes.

51. A process for making up the lips, the face or the eyelids, comprising moistening the surface of an aqueous solid composition according to claim 10 with water and applying said partially rehydrated composition to the lips, the face or the eyelids.

* * * * *

UNITED STATES PATENT AND TRADEMARK OFFICE
CERTIFICATE OF CORRECTION

PATENT NO. : 6,045,814
DATED : April 4, 2000
INVENTOR(S) : Véronique ROULIER, et al.

It is certified that error appears in the above-indentified patent and that said Letters Patent is hereby corrected as shown below:

In claim 38, column 13, line 48, delete "p1".

In claim 39, column 13, line 56, "mpa·s" should read --mPa·s--.

In claim 47, column 14, line 21, "In" should read --in--, and "riaid" should read --rigid--.

Signed and Sealed this

Twentieth Day of March, 2001

Attest:

NICHOLAS P. GODICI

*Attesting Officer*     *Acting Director of the United States Patent and Trademark Office*